United States Patent [19]
Reduto

[11] Patent Number: 6,111,639
[45] Date of Patent: Aug. 29, 2000

[54] METHOD AND APPARATUS FOR COUNTERING ADVERSE DRUG EVENTS

[76] Inventor: Lawrence A. Reduto, 125 Tall Oak Crescent, Syosset, N.Y. 11791

[21] Appl. No.: 09/073,384

[22] Filed: May 6, 1998

[51] Int. Cl.$^7$ ........................................................ G01J 3/00
[52] U.S. Cl. .......................... 356/300; 356/302; 356/303; 356/319
[58] Field of Search .................................... 356/300, 302, 356/303, 319

[56] References Cited

U.S. PATENT DOCUMENTS

| | | |
|---|---|---|
| 5,229,362 | 7/1993 | Kirst et al. .................................... 514/9 |
| 5,267,178 | 11/1993 | Berner . |
| 5,298,428 | 3/1994 | O'Rourke et al. . |
| 5,400,138 | 3/1995 | Peterson et al. . |
| 5,468,224 | 11/1995 | Souryal . |
| 5,510,621 | 4/1996 | Goldman . |
| 5,563,031 | 10/1996 | Yu . |

*Primary Examiner*—Robert Kim
*Assistant Examiner*—Reginald A. Ratliff
*Attorney, Agent, or Firm*—Scully, Scott Murphy & Presser

[57] ABSTRACT

A method and apparatus for counteracting adverse drug events (ADE's) which are caused by the administration of intravenous medications of incorrect types, concentrations or dosages, and which may result in morbidity and even mortality to recipient patients. A container, preferably in the nature of a transparent plastic bag employed for intravenous administrations, contains the requisite infusion at a prescribed volume, adding a specified amount of prescribed medication possessing a predefined amount of a coloring material, such as a vegetable dye, to the volume of infusion material or liquid in order to form a prescribed concentration of medication, with the coloring material defining a specific type of medication. Analyzing of the concentration of medication is effected through the utilization of spectrophotometric equipment, and to resultingly obtain a real medication concentration value. Thereafter, a comparison is carried out between the real or actual and the prescribed medication concentration values, and an indicator, such as a label or the like, is generated for placement on the intravenous container which is indicative of the type and verified concentration of the medication in the infusion. This procedure, in effect, by being implemented at the pharmacy level, provides for medication and concentration verification prior to administering the medication intravenously to a patient, and by verifying the presence of the indicator on the intravenous (IV) container, or by using a spectrophotometer at a nurse station in order to again verify the medication and its concentration as a check or safeguard preceding administration thereof to the patient.

16 Claims, 2 Drawing Sheets

METHOD AND APPARATUS FOR COUNTERING ADVERSE DRUG EVENTS

BACKGROUND OF THE INVENTION

1. Field of the Invention

The present invention relates to a method for counteracting adverse drug events (ADE's) which are caused by the administration of intravenous medications of incorrect types, concentrations or dosages, and which may result in morbidity and even mortality to recipient patients. The invention is further directed to an apparatus for the counteraction of adverse drug events of the types described herein.

In accordance with current statistics which have been compiled by the Institute for Health Care Improvement, adverse drug event injuries caused by the intravenous administering of incorrect or improperly dosed and/or concentrated medications are a major cause of disabilities encountered by hospitalized patients. In the United States alone, adverse drug event effects are considered to affect as many as 770,000 to possibly two million patients annually, at costs which are estimated to be approximately 4.2 billion dollars, with as many as half of all adverse drug event injuries being considered as having been caused by administering errors and, consequently, deemed to be preventable in nature. These errors in the improper or erroneous intravenous administration of medication are calculated to engender costs of approximately $4,685.00 for each patient, and to increase the average length of a hospital stay by two days, with such adverse drug event injuries being normally encountered in virtually every hospital or similar health related facility.

The majority of serious injuries resulting from adverse drug events pertain to the utilization of intravenous medications which are added to an infusion of dextrose in water or saline solution. Unless a patient is highly allergic, one or two doses of an erroneously administered oral medication would be unlikely to result in significant morbidity, whereas, on the other hand, a single dose of an intravenous medication; for example, such as potassium, could be fatal in nature if inadvertently administered to a patient who is subject to renal failure. The vast majority of intravenous additives are clear and colorless, as a result of which it is not readily possible to ascertain as to whether the proper medication or dosage of such medication was, in fact, added to the infusion. Basically, the only mechanism available for the prevention of errors is the basic assumption that the pharmacist has added the appropriate medication in the prescribed dosage to the infusion. Other potential errors can occur through the use of current methods of intravenously administrating such medications, in that the pharmacist, upon having added the medication, causes a label to be placed on the bag of the infusion with the name and dosage or degree of dilution of the medication. The label can conceivably fall off, be smudged or misinterpreted by a nurse or other medical personnel administering the infusion to the patient, with the resultant potential of an adverse drug event.

Although steps have been taken to minimize many of the potential errors caused by adverse drug events through joint efforts by the Food and Drug Administration, hospitals and the pharmaceutical industry, it would be highly advantageous to provide for the standardization of commonly utilized and potentially harmful additives. Among recent efforts are the color coding of these agents with food coloring, and the use of spectrophotometers to determine the nature and concentrations of the additives, with such technology being relatively inexpensive and commonly employed throughout industry and in medical laboratories. Thus, currently, various aspects of the technology which can be potentially applied to solving or at least considerably ameliorating the problems encountered with regard to adverse drug event injuries, can be ascertained in the state-of-the-art.

2. Discussion of the Prior Art

Among publications which are of interest with regard to the present inventive concept which is directed to eliminating or at least reducing the phenomenon of adverse drug events caused by the administration of intravenous medications of various types, concentrations or dosages; of particular interest is U.S. Pat. No. 5,468,224 to Souryal. This particular patent teaches the color coding of injectable medications which are most frequently intravenously administered, particular in the presence of emergency situations in which time is of the essence or critical in nature so as to necessitate immediate medical decisions. The injectable medications are color coded through the addition of harmless coloring materials to the medications, such as food coloring agents, wherein each particular medication is assigned a specific standardized color or, alternatively, a particular class of medications is assigned a specific color. In this particular instance, the patent does not teach or take into consideration the concentration of such injectable medication based on color concentrations, and this would not preclude the inadvertent infusion of dosages of medications which have been incorrectly added to an infusion of a saline or similar basic infusion.

U.S. Pat. No. 5,510,621 to Goldman discloses the utilization of an analyzer employing near-infrared spectrophotometric techniques for determining the concentration of colorless components used in the make-up of an infusion, such as parenteral nutrients,; e.g., in an intravenous bag. However, in this particular patent there is also a brief but undeveloped suggestion that spectrophotometric techniques in the visible light region can be used to determine concentrations of material. Other spectrophotometric and spectroscopic methods have been employed in various modes in order to determine concentrations of colored chemical samples and physiological samples; for example, in blood or other liquid media; referring for instance, to U.S. Pat. No. 4,193,694 to Smith; U.S. Pat. No. 4,935,875 to Shah et al.; and U.S. Pat. No. 4,997,769 to Lundsgaard. None of these patents teach the utilization or requirement of the addition of dye materials in order to facilitate photometric concentration analysis.

U.S. Pat. No. 5,563,031 to Yu discloses the use of adding a dye coupling compound in a reagent system having an analyte whose presence is to be measured and which reacts to form colored chromophores in amounts indicative of the quantity of the analyte contained in the system.

U.S. Pat. No. 5,298,428 to O'Rourke, et al. teaches that non-photoreactive chemical samples whose concentrations are to be determined can be readily mixed with an indicative dye so as to render them photoreactive, and thereby consequently facilitating the determination of their concentrations utilizing spectrophotometric techniques.

Finally, of general interest are the disclosures of U.S. Pat. Nos. 5,267,178 to Berner and 5,400,138 to Peterson, et al. which, respectively, describe computer control techniques and intelligent spectrophotometric devices employed for color measurement purposes.

Although coloring materials for medications have been employed in order to assist medical personnel in emergency situations, to date there has not yet been derived an effective method for safeguarding against adverse drug event (ADE) injuries, nor has there been any suggestion or disclosure of employing the addition of coloring materials to medications for utilization in intravenous administrative applications in order to verify the concentration of a desired medication.

SUMMARY OF THE INVENTION

Accordingly, pursuant to the present invention there is contemplated the provision of a method and an apparatus for eliminating or at least considerably reducing the phenomenon of adverse drug events (ADE's) caused by the administration of intravenous medications of incorrect types, erroneous concentrations or dosages. To that effect, the invention provides for a container, preferably in the nature of a transparent plastic bag employed for intravenous administrations, containing the requisite infusion at a prescribed volume, adding a specified amount of prescribed medication possessing a predefined amount of a coloring material, such as a vegetable dye, to the volume of infusion material or liquid in order to form a prescribed concentration of medication, with the coloring material defining a specific type of medication. Analyzing the concentration of the medication is effected through the utilization of spectrophotometric equipment, and to resultingly obtain a real medication concentration value. Thereafter, a comparison is carried out between the real or actual and the prescribed medication concentration values, and an indicator, such as a label or the like, is generated for placement on the intravenous container which is indicative of the type and verified concentration of the medication in the infusion. This procedure, in effect, by being implemented at the pharmacy level, provides for medication and concentration verification prior to administering the medication intravenously to a patient, and by verifying the presence of the indicator on the intravenous (IV) container, or by using a spectrophotometer at a nurse station in order to again verify the medication and its concentration as a check or safeguard preceding administration thereof to the patient.

Accordingly, it is an object of the present invention to provide a method for the reduction of adverse drug events which are caused by the inadvertent administration of intravenous medications of potentially incorrect types, concentrations or dosages.

Another object of the present invention resides in the provision of a method for reducing the occurrence of adverse drug events by analyzing the contents of intravenous containers containing the prescribed medication incorporating predefined amounts of coloring materials through spectrophotometric procedures, and thereafter identifying the contents of the intravenous container prior to the intravenous administration thereof to a patient.

Still another object of the present invention resides in the provision of a method for reducing adverse drug events through the utilization of a spectrophotometric analysis of the contents of intravenous containers having prescribed concentrations of medications including identifying coloring material, and wherein identifying labels are generated and adapted to be applied to the intravenous container responsive to ascertaining that the correct dosage and concentration of medication is contained therein.

Yet another object of the present invention resides in the provision of an apparatus for analyzing the contents of intravenous containers having quantities of medications therein, and wherein a spectrophotometric analysis provides indication as to the correctness of the dosage and concentration of the medication, and facilitate generating identifying indicia or labels applicable to the intravenous container in order to verify the contents thereof.

BRIEF DESCRIPTION OF THE DRAWINGS

Reference may now be had to the following detailed description of an exemplary embodiment of the invention, taken in conjunction with the accompanying drawings; in which.

DETAILED DESCRIPTION OF A PREFERRED EMBODIMENT

Figure 1:
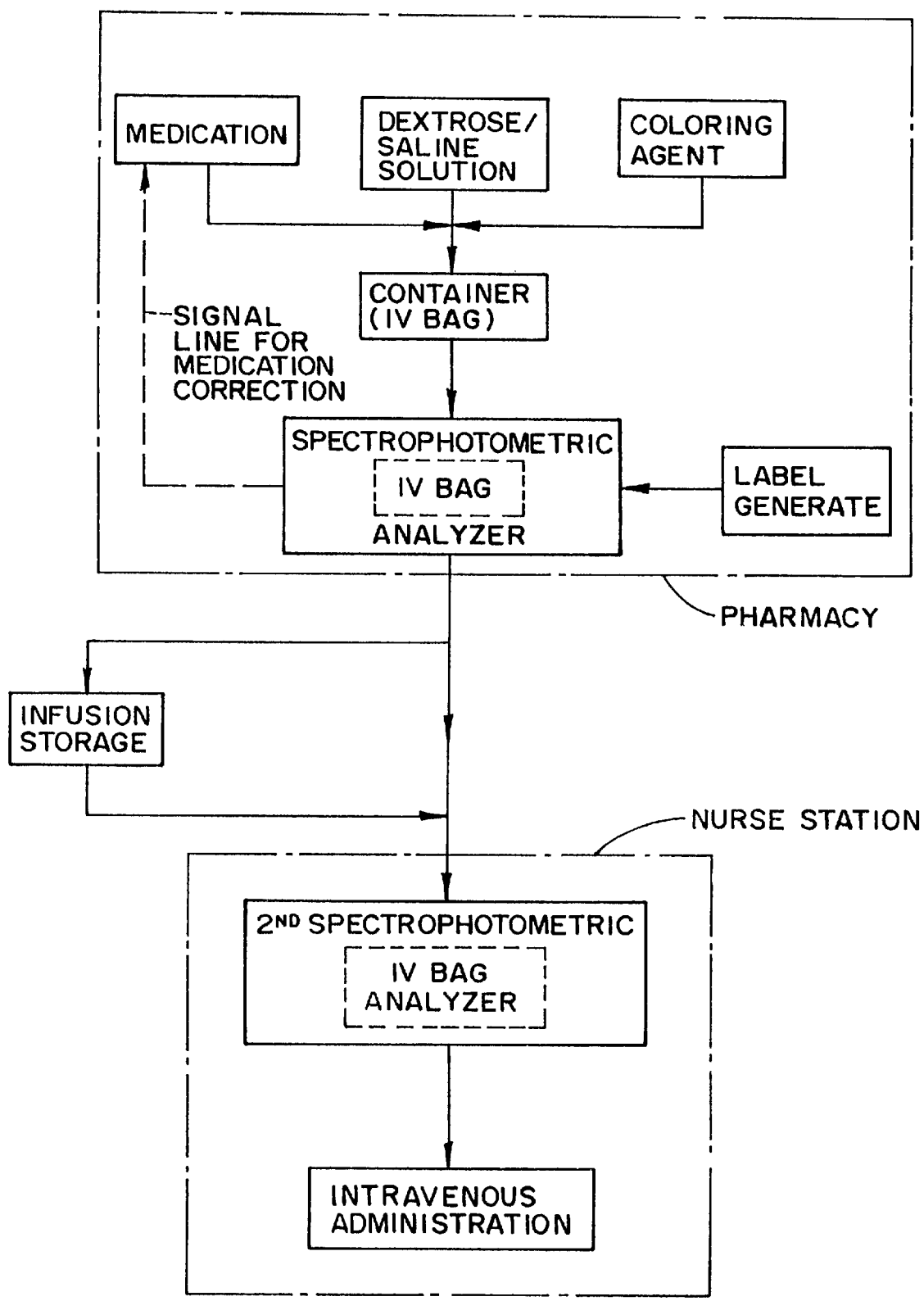
FIG. 1 illustrates a typical flow chart illustrative of the method and procedure for reducing the phenomenon of adverse drug events caused by the administration of incorrect intravenous medications.

Referring now specifically to the drawings, and particularly to FIG. 1, there is represented a flow chart concerning the preparation and analysis of an intravenous medication prior to administration thereof to a patient, a pharmaceutical preparate of a prerequisite dosage and concentration is dispensed (by a pharmacist) from a suitable supply source into a container having an infusion of a dextrose in water or saline solution therein, which container may be a transparent flexible plastic IV bag, as widely employed in hospitals and other health-related facilities for the intended intravenous administration of the prescribed medication or pharmaceutical to a patient.

Prior to the infusion with the medication being sealed into the container or intravenous bag, a suitable coloring agent, such as a vegetable dye which has been approved by the Food and Drug Administration (FDA) is added to the contents of the IV bag, with the coloring agent being coded to provide identifying data relative to a particular medication; for example, assuming the latter is potassium chloride, it is colored red by the addition of a specified food coloring as mandated by the Food and Drug Administration. Different types or classes of medications may be imparted different colorings in conformance with specific mandated requirements.

The infusion containing the medication and coloring agent in the solution is then conveyed while contained in the intravenous bag to a spectrophotometer for the implementation of a spectrographic analysis, by means of which there is determined the concentration and dosage of the medication in the infusion, i.e. contents of the IV bag. If necessary, in order to attain a specifically mandated or required concentration of the medication as prescribed by a physician, an additional amount of medication may be added to the contents of the intravenous bag until the spectrographic analysis meets and satisfies the particular requirements set for the concentration of the medication within the container or IV bag.

Thereafter, as required a bag content-identifying label may be generated, the latter of which may also be color coded in conformance with the contents of the bag, and is adhesively applied to the exterior of the intravenous bag, thereby providing information as to the contents of the bag, as to the dosage and type of medication and the concentration thereof, so as to preclude any error occuring in the intravenous administration of the medication to a patient.

From the label generating station, the intravenous bag with the contents may be either conveyed to a suitable storage area, or directly forwarded to a nurse station or the like to enable the intravenous administration thereof to a patient. Prior to administering the foregoing to a patient, the intravenous bag and the contents may be again subjected to spectrographic analysis to ascertain that the correct contents are contained therein in conformance with the label which has been previously applied thereto, thereby avoiding any errors in the administration of the medication which could lead to an injury or possibly even the death of the patient.

Figure 2:
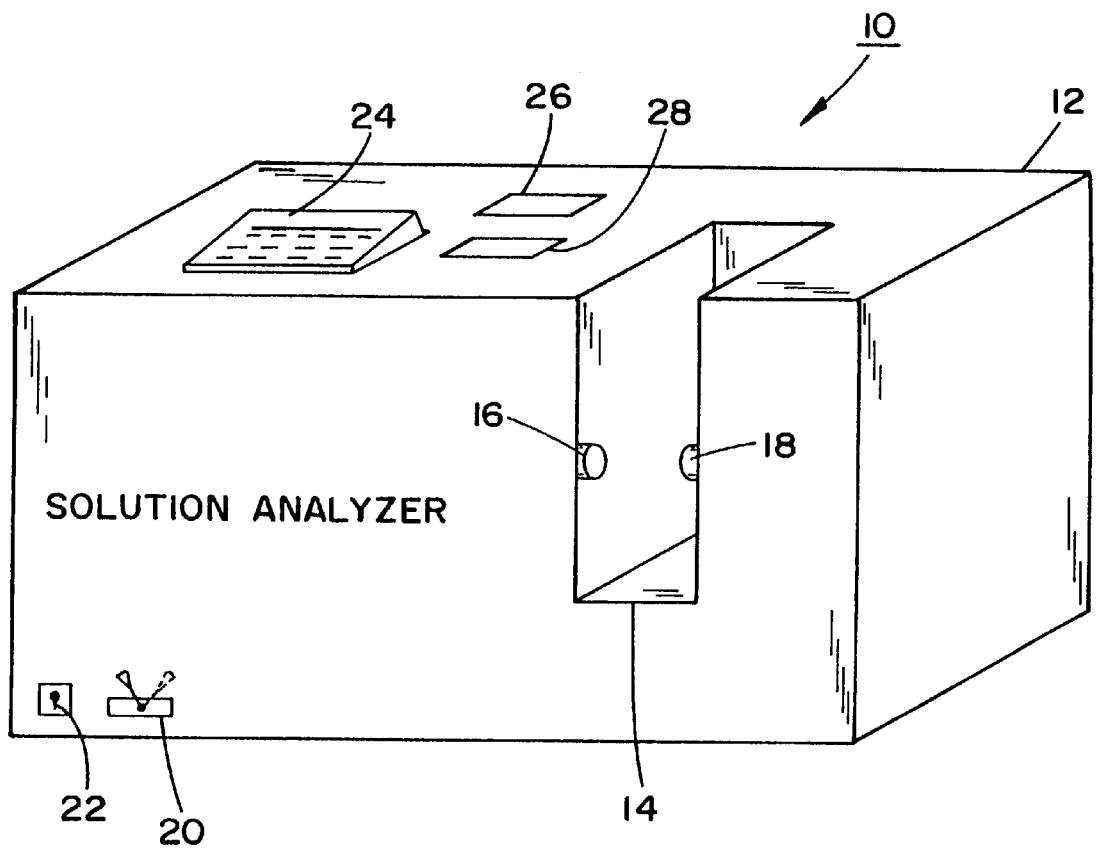
FIG. 2 illustrates, generally diagrammatically, a spectrophotometric apparatus for analyzing medications contained in an intravenous container prior to the administration thereof to a patient.

As illustrated in FIG. 2 of the drawings in a generally diagrammatic manner, a solution analyzer 10 for spectrophotometrically analyzing a solution containing a medication and an identifying coloring agent may consist of a suitable cabinet or housing 12 having a slot or bin 14 into which there may be inserted an intravenous bag or container with its contents. A light source 16 and a photocell 18 are arranged on opposite sides of the bin for implementing a photometric analysis of the contents of he container or IV bag. The cabinet 12 may be quipped with a suitable on/off switch 20 which may be activated only at a period in time when an analysis is to be carried out with regard to the contents of the intravenous bag, and the analyzer is controlled by a suitable key 22 operated by a pharmacist who is in charge of preparing the medication for intravenous administration.

A computer keyboard 24 may be mounted on the cabinet for the inputting of any required information concerning the concentration and dosage for the medication in the intravenous bag, and an LED (light emitting diode) 26 is provided for a display of the medication type or class, with a further LED 28 being provided for the display of the dosage on the analyzer. Upon the analysis having been effected by passing a light from the light source 16 to the photocell 18 through the transparent intravenous bag containing the medical solution, if indication is given that the latter is correct as to the dosage and concentration, it is possible to have the analyzer generate a label by means of a suitable apparatus, for application to the intravenous bag and providing pertinent information as to its contents.

By way of example, the following can be contemplated in implementing the inventive method of eliminating or reducing adverse drug events:

Thusly, a manufacturer of heparin would add a certain amount of a coloring agent, such as FDC No. 18 to each vial of concentrated heparin. The label colors themselves which are to be generated could be also standardized, and would correspond with the color of the additive contained in the intravenous bag. The next step in utilizing the method would be the use of a spectrophotometer, which is a constituent of the analyzer as illustrated in FIG. 2 of the drawings, in order to determine the nature and concentration of an additive. The technology is relative inexpensive and may be commonly employed in industry, in hospitals or medical laboratories, respecting which the analyzer would be utilized as follows:

Assuming that an infusion containing potassium chloride is red in color due to the addition of a specified food coloring as mandated by the FDA (Food and Drug Administration). Different concentrations of potassium would have different color shadings and therefor would have different ranges in wavelengths of light. In order to provide or produce an infusion of potassium, the pharmacist would read the physician's order and type in the drug and the order concentration (for example 10 mEq/L, 20 mEq/L; etc.) into a keyboard 24 on the analyzer 10. The pharmacist would then add the drug to the bag of intravenously-administrable dextrose or saline. The color of the solution would remain the same irrespective as to whether it is a 250 ml, 500 ml or 1000 ml intravenous bag. The intravenous bag or container is then placed in the analyzer 10, particularly in the slot portion identified as the bin 14. The photocell 18 then "reads" the color of the bag. The analyzer would then interpret the constituents of the bag contents and concentration thereof and display these values. The analyzer would then also be equipped with a structure which enables generating a label for identifying the contents of the bag of intravenous fluid. Unless there is a concordance between the drug or medication and the concentration typed in by the pharmacist and the interpretation obtained from the analyzer, the label for the bag is not generated, and without the label on the bag, the nurse will be cautioned not to administer the infusion. As a result of the foregoing, the pharmacist, the equipment comprising the analyzer and the nurse also all serve to ensure that the drug additives and its concentration are correct in nature. Currently, reliance is only placed on the pharmacist to add the correct dosage of the correct medication, whereas with the foregoing this provides an assurance that the method and apparatus will create the correct medication and dosage for administration to a patient.

Inasmuch as only 8 or 10 colors are employed for commonly administered intravenous medications, a nurse could easily determine whether heparin or lidocaine (for example) was being infused in the proper dosages and concentration by again checking the bag contents in a similar analyzer at the nurse station prior to administering to a patient. This also serves as an additional safety or precautionary check on the process pursuant to the invention so as to prevent adverse drug events.

The cost involved to the health care industry in the implementation of such a system is minimal, particularly inasmuch as the cost of an analyzer and spectrophotometer represents only a one time purchase, and the cost of adding a food coloring or additive to a vial of medication is considered to be relatively insignificant in nature. Similarly, any changes in the color coding of the vials or ampoules of medication can be accomplished at minimal cost.

As previously indicated, the present invention can be utilized primarily for commonly employed medications (potassium, heparin, lidocaine, insulin (not affecting the vials of insulin used by patients), epinephrine, dopamine, dobutamine, nitroprusside and nitroglycerin. Additional agents which are to be infused could be added at any time, and would simply necessitate the reprogramming of a microprocessor located in the analyzer.

While there has been shown and described what is considered to be a preferred embodiment of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A method of testing the dosage and concentration of a medication in a solution containing a coloring agent identifying the type or class of medication; comprising:

(a) introducing said medication into a solution of dextrose in water or saline solution; adding an identifying coloring agent to said solution so as to form an intravenously administrable infusion;

(b) conveying a specified quantity of said infusion into a generally transparent container; and (c) imparting a spectrophotometric analysis to the infusion in said container so as to determine the dosage and concentration of said medication in said container.

2. A method as claimed in claim 1, wherein the results of said spectrophotometric analysis are compared with preset parameters for the dosage and concentration of the medication in said infusion to provide indication of the correctness of said dosage and concentration.

3. A method as claimed in claim 2, wherein identifying indicia for said container is generated upon verification of the correctness of the dosage and concentration of the medication in the infusion in said container.

4. A method as claimed in claim 3, wherein said identifying indicia comprises a label attachable to said container.

5. A method as claimed in claim 4, wherein said label is color-coded in correlation with the type or class of the medication in said infusion.

6. A method as claimed in claim 1, wherein said container comprises a flexible IV bag.

7. A method as claimed in claim 1, wherein a further spectrophotometric analysis is implemented to said infusion prior to intravenous administration to a patient to verify the correctness of the dosage and concentration of the medication of in said container in conformance with preset values for said dosage and concentration.

8. An apparatus for testing and analyzing the dosage and concentration of a medication in a solution containing a coloring agent identifying the type or class of medication; comprising:

(a) means for introducing said medication into a solution of dextrose in water or saline solution; adding an identifying coloring agent to said solution so as to form an intravenously administrable infusion;

(b) means for conveying a specified quantity of said infusion into a generally transparent container; and (c) means for imparting a spectrophotometric analysis to the infusion in said container so as to determine the dosage and concentration of said medication in said container.

9. An apparatus claimed in claim 8, wherein the apparatus comprises means for comparing the results of said spectrophotometric analysis with preset parameters for the dosage and concentration of the medication in said infusion to provide indication of the correctness of said dosage and concentration.

10. An apparatus as claimed in claim 9, wherein said apparatus comprises means for generating identifying indicia for said container upon verification of the correctness of the dosage and concentration of the medication in the infusion in said container.

11. An apparatus as claimed in claim 10, wherein said identifying indicia comprises a printed label attachable to said container.

12. An apparatus as claimed in claim 11, wherein said label is color-coded in correlation with the type or class of the medication in said infusion.

13. An apparatus as claimed in claim 8, wherein said container comprises a flexible IV bag.

14. An apparatus as claimed in claim 8, wherein a further spectrophotometric apparatus implements a subsequent analysis to said infusion prior to intravenous administration to a patient to verify the correctness of the dosage and concentration of the medication of in said container in conformance with preset values for said dosage and concentration.

15. An apparatus as claimed in claim 8, wherein a computer keyboard is mounted on said apparatus for inputting specified parameter for said infusion and for enabling a comparison with a real infusion in said container.

16. An apparatus as claimed in claim 8, wherein said apparatus includes displays for the type and concentration of the medication in said container.

* * * * *